US00PP26208P3

(12) United States Plant Patent
Pierron-Darbonne

(10) Patent No.: US PP26,208 P3
(45) Date of Patent: Dec. 15, 2015

(54) STRAWBERRY PLANT NAMED 'DELUXE'

(50) Latin Name: *Fragaria×ananassa*
Varietal Denomination: Deluxe

(71) Applicant: Darbonne Pepiniere, SAS, Le Barp (FR)

(72) Inventor: Alexandre Pierron-Darbonne, Navarra (ES)

(73) Assignee: DARBONNE PEPINIERE, SAS (FR)

( * ) Notice: Subject to any disclaimer, the term of this patent is extended or adjusted under 35 U.S.C. 154(b) by 27 days.

(21) Appl. No.: 13/987,146

(22) Filed: Jul. 3, 2013

(65) Prior Publication Data

US 2015/0020247 P1 Jan. 15, 2015

(30) Foreign Application Priority Data

Jul. 5, 2012 (QZ) ..... 2012/1502

(51) Int. Cl.
*A01H 5/08* (2006.01)

(52) U.S. Cl.
USPC ..... Plt./208

(58) Field of Classification Search
USPC ..... Plt./208
CPC ..... A01H 5/0893
See application file for complete search history.

(56) References Cited

FOREIGN PATENT DOCUMENTS

| | | |
|---|---|---|
| CH | 13-2900 | 9/2013 |
| ES | 20120163 | 6/2012 |
| QZ | 2012/1502 | 5/2012 |

OTHER PUBLICATIONS

UPOV Record Detail 2012.*
"Planasa presenta dos nuevas variedades de fresa" dated Aug. 30, 2013, downloaded from Fresh Plaza on the world wide web at www.freshplaza.es/article/75890/Espa%C3%B1a-PLANASA-presenta-dos-nuevas-variedades-de-fresa (with English translation).
"La variedad de Planasa, Dream, triunfa en SIVAL 2013 Jan. 21, 2013" dated Jan. 21, 2013, downloaded from Planasa on the world wide web at www.planasa.com/index.php?m=48&subm=58&id=85&pagina=7 (with English translation).

* cited by examiner

*Primary Examiner* — Keith O. Robinson
(74) *Attorney, Agent, or Firm* — Knobbe, Martens, Olson & Bear, LLP

(57) ABSTRACT

A new and distinct strawberry variety, *Fragaria×ananassa,* cv. 'Deluxe' is characterized by an orange red fruit color, a fruit shape that ranges from round to conical, a medium leaf size, and a medium green color of the upper side of the leaf.

11 Drawing Sheets

Latin name of the genus and species claimed: *Fragaria× ananassa.*

Variety denomination: 'Deluxe'.

BACKGROUND AND SUMMARY OF THE INVENTION

The present invention relates to a new and distinct strawberry variety. The varietal denomination of the new variety is 'Deluxe'. The new variety was designated by the breeder as 'Deluxe (DA46)'. The new variety of strawberry was created in a breeding program by crossing two parents in 2004 in Le Barp, France; in particular, by crossing as seed parent an undistributed strawberry parent designated "16.01.18" (unpatented) and as pollen parent an strawberry parent designated 'Darselect' (U.S. Plant Pat. No. 10,402). Seed parent is a selection from breeder's program and has not been commercialized.

The resulting seedling of the new variety was grown and asexually propagated by runners in Le Barp, France 0.7° W., 44°, 50 meters elevation. Propagation by runners included propagation by runners, separately for each varieties, first into a Screen-House, and after in the fields. Clones of the new variety were further asexually propagated and extensively tested. Each variety was reproduced by stolons in the nurseries. In order to establish and bring to health the initial head clones, mother plants that had developed several several stolons were subjected to a heat treatment, or Thermoterapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing has demonstrated that the combination of traits disclosed herein which characterize the new variety are fixed and retained true to type through successive generations of asexual reproduction.

Among the characteristics which appear to distinguish the new variety from its closest variety of which I am aware (which is also the pollen parent of the new variety), 'Darselect' is a combination of traits which include: a medium leaf size, as compared to a large leaf size for 'Darselect', a medium green color of the upper side of the leaf (RHS green group color near 139 A to 141 A), as compared to light green for 'Darselect', an orange red fruit color (RHS orange-red group near 33 B to 33 A) as compared to red (RHS red group near 45A to 44 B) for "'Darselect', and a fruit shape that ranges from round to conical, as compared to conical for 'Darselect'. The new variety is distinguished therefrom its parents by the following characteristics possessed by 'Deluxe' which are different than, or not possessed, by the seed parent designated designated "16.01.18" (unpatented).

(1) Seed parent "16.01.18" (unpatented) is less vigorous than the plant of the new variety "Deluxe". (2) In seed parent "16.01.18" (unpatented) the color of the leaves is lighter than in the new variety "Deluxe".

On May 7, the average fruit mass (g/fruit) observed for the new variety 'Deluxe' was 32.4 g, as compared to 24.5 g for 'Darselect'. The luminosity for the fruit of the new variety at 460 nm was 62.5, as compared to 51.2 for 'Darselect'.

Characteristics which appear to distinguish the new variety from the variety 'Clery', at least include that the new variety has an average fruit mass of 32.4 g and a luminosity at 460 nm of 62.5, as compared to an average fruit mass of 18.9 g and luminosity at 460 nm of 43.5 for 'Clery'. In the USA, 'Clery' is an unpatented variety. In The European Union, 'Clery' patented as: EU 16743.

BRIEF DESCRIPTION OF PHOTOGRAPHS

The accompanying photographs show typical specimens of the new variety, designated 'Deluxe' or 'DA 46' in the illustrations, including fruit, foliage and flower, in color as nearly true as it is reasonably possible to make in color illustrations of this character.

DESCRIPTION OF THE NEW VARIETY

Figure 1:
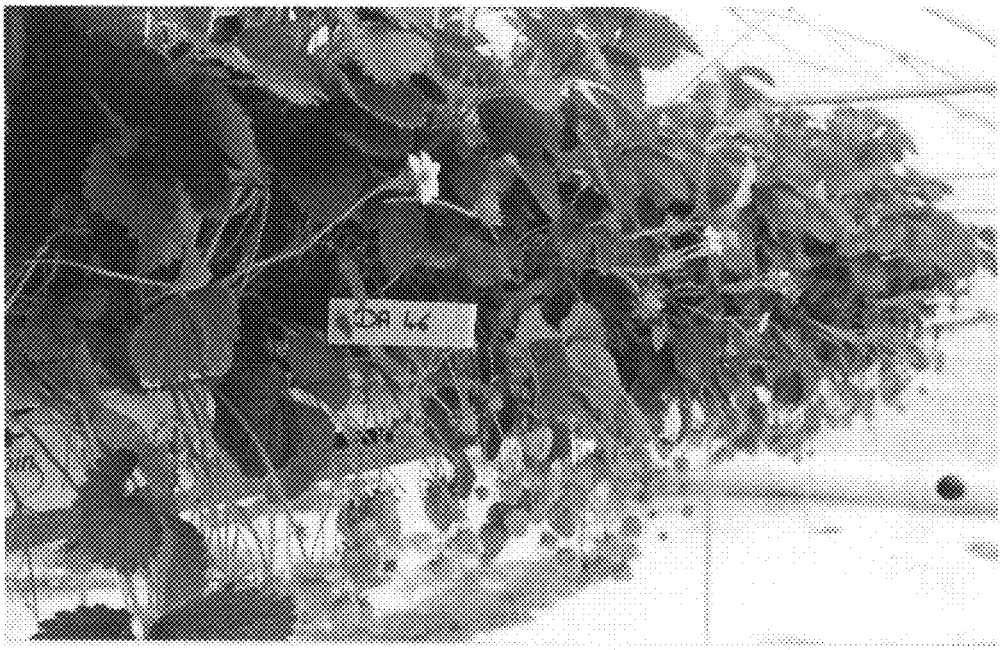
FIG. 1 shows several plants of the new variety 'Deluxe'.
Figure 2:
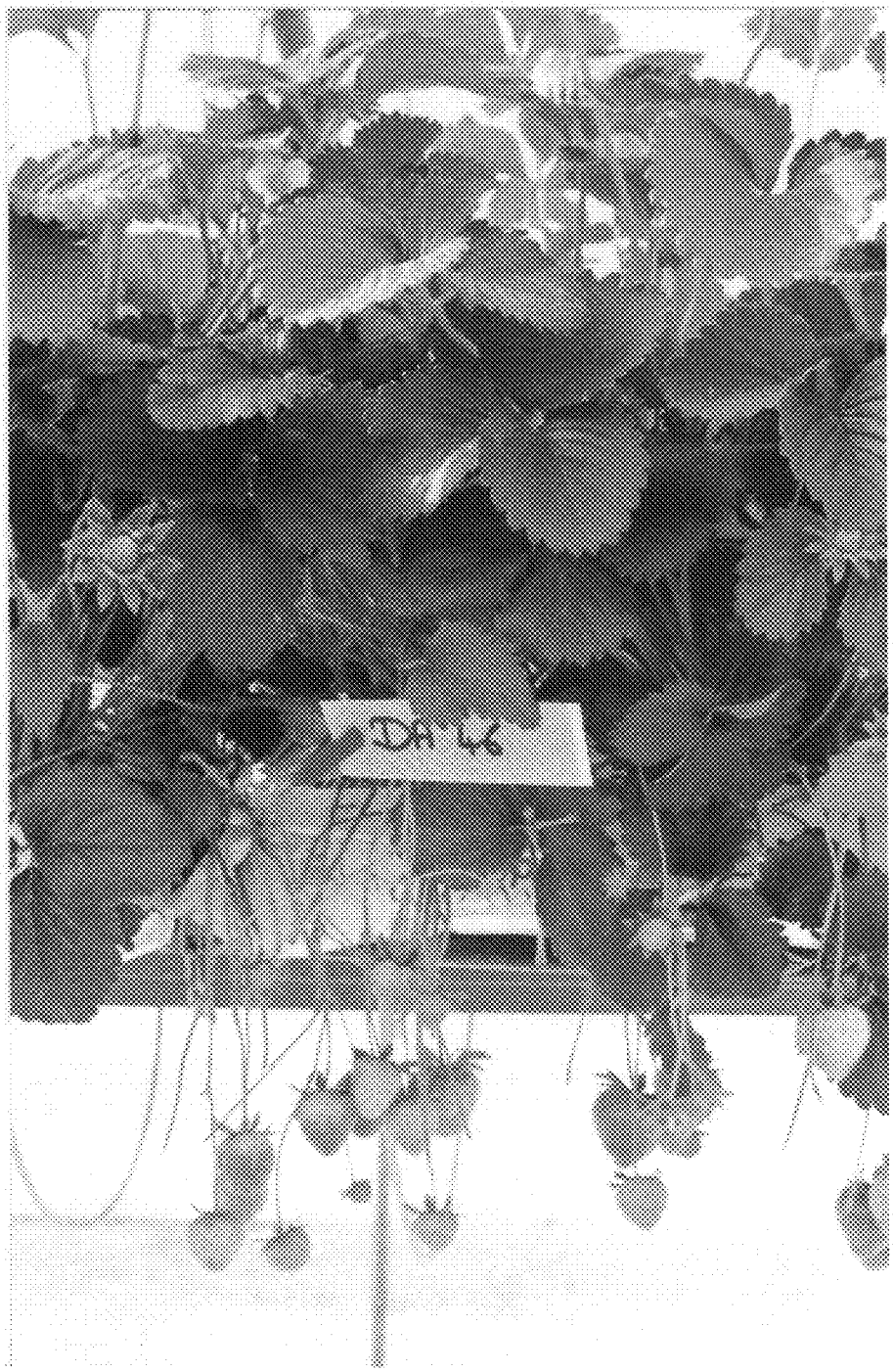
FIG. 2 shows several plants of the new variety 'Deluxe'.
Figure 3:
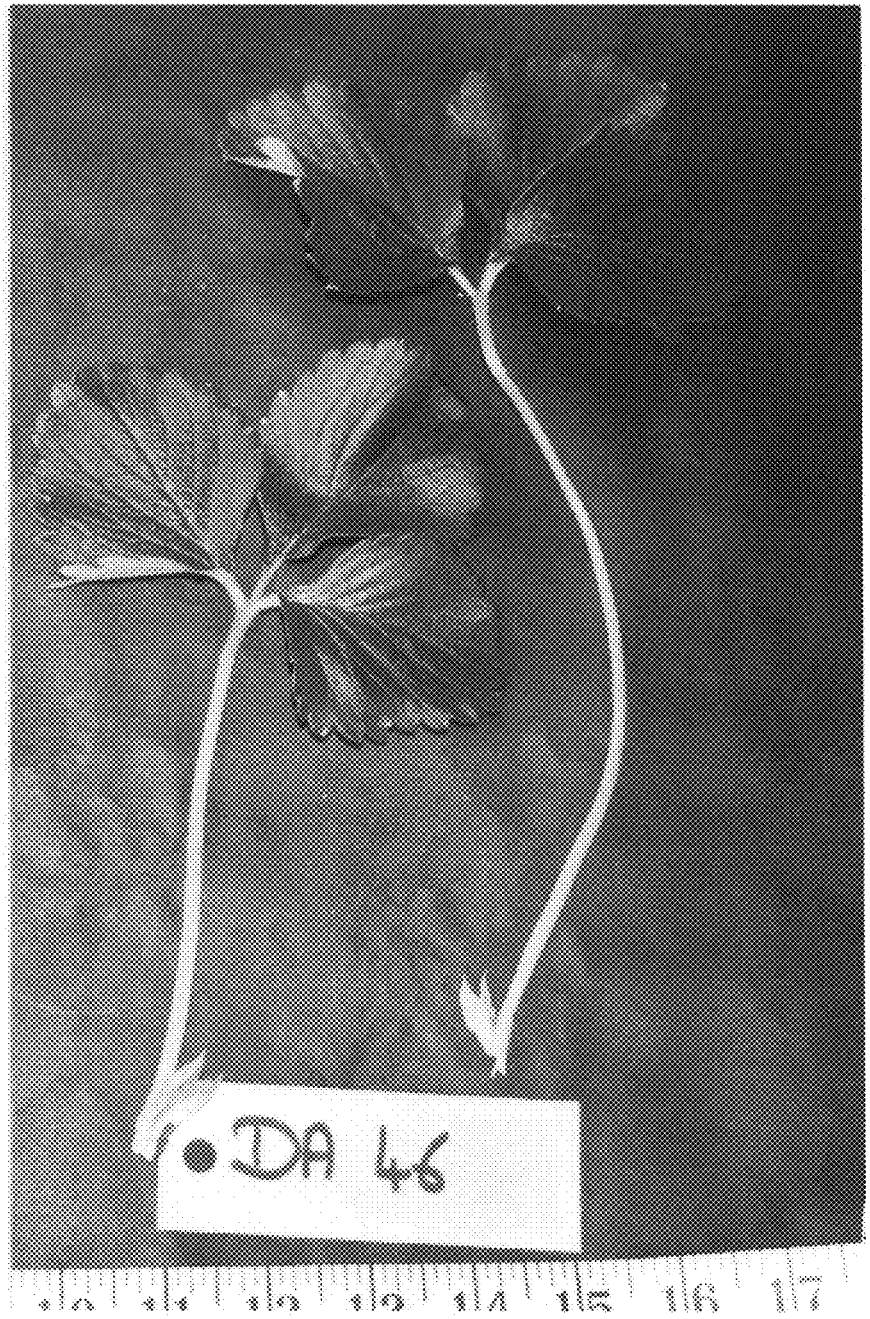
FIG. 3 shows the upper side of a complete leaf of the new variety 'Deluxe'. A medium leaf size, medium green color (RHS green group color near 139 A to 141 A), and strongly concave to slightly concave cross-section can be seen.
Figure 4:
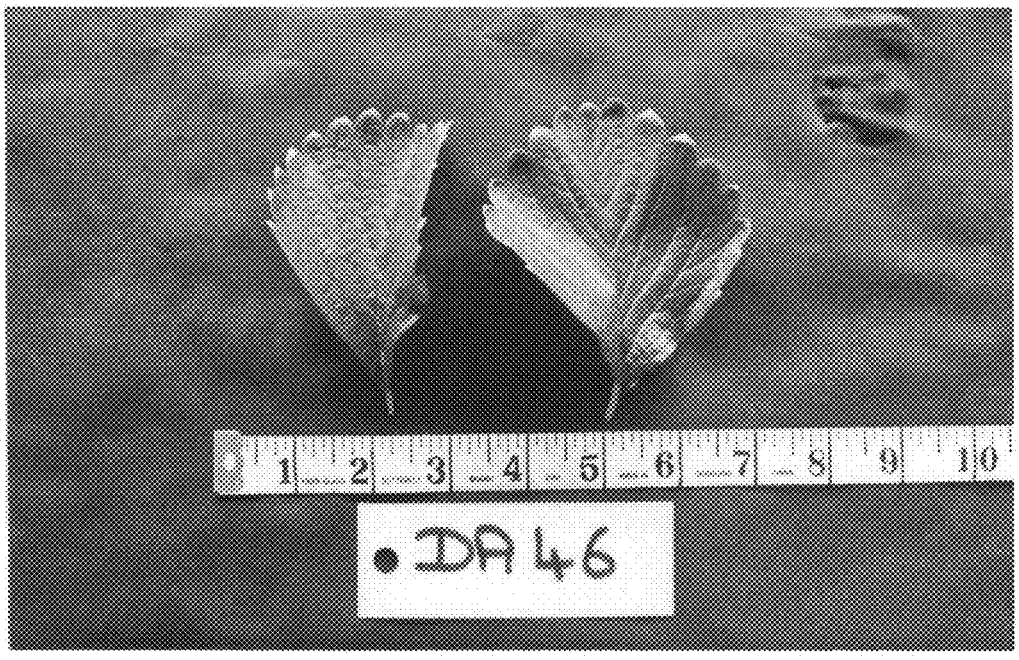
FIG. 4 shows the upper side of a terminal leaflet of the new variety 'Deluxe'. A medium green color (RHS green group color near 139 A to 141 A), and serrate shape of incisions of the margin of the terminal leaflet can be seen.
Figure 5:
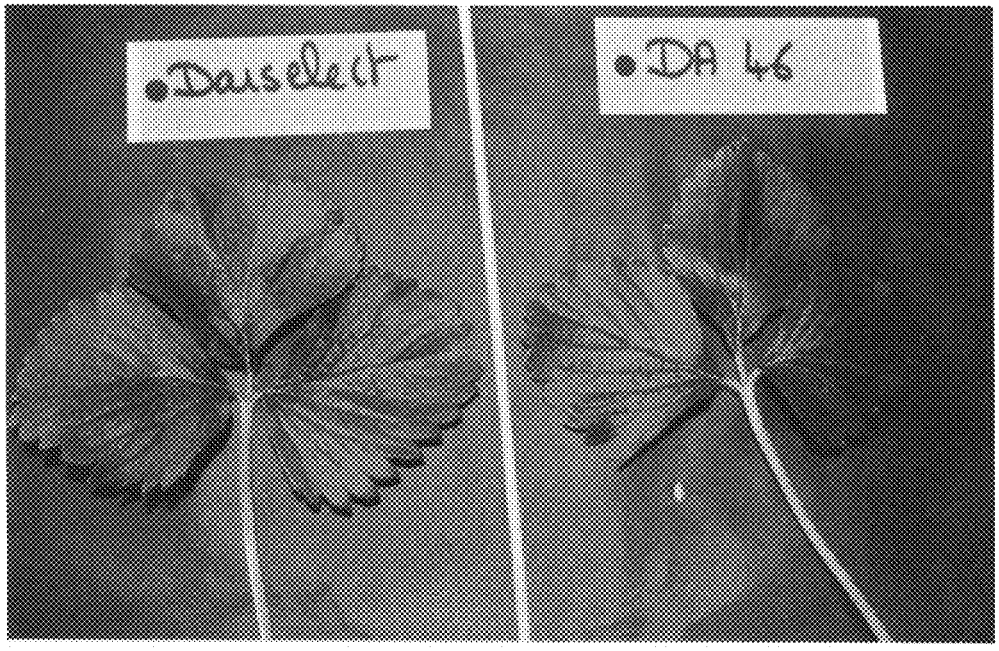
FIG. 5 shows a comparison of the upper side of a complete leaf of the new variety 'Deluxe' to that of the pollen parent, 'Darselect'. A medium leaf size, and medium green color (RHS green group color near 139 A to 141 A) can be seen in the new variety, as compared to a large leaf size and light green color for 'Darselect'.
Figure 6:
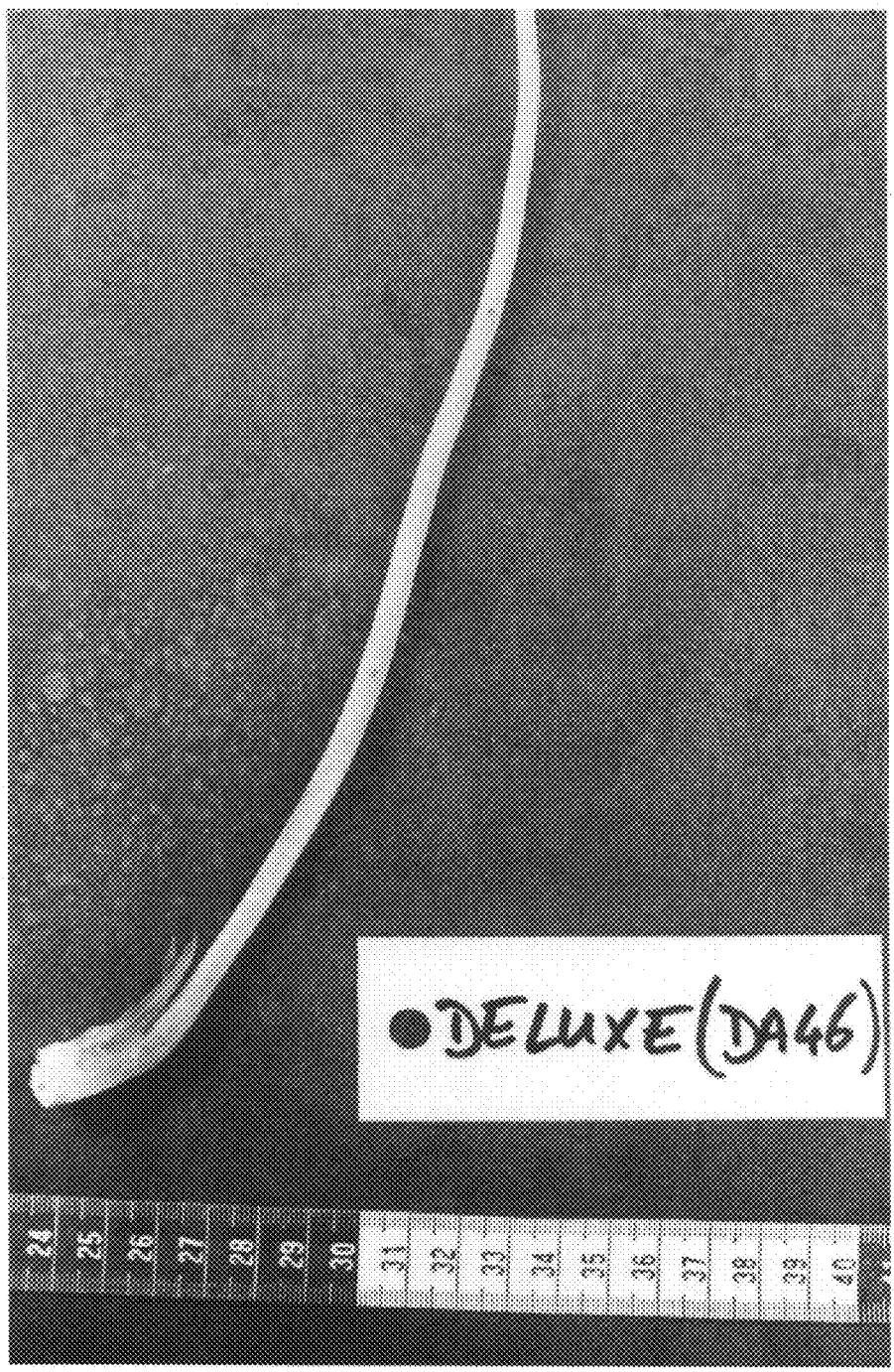
FIG. 6 shows the stipule and petiole of the new variety, 'Deluxe'.
Figure 7:
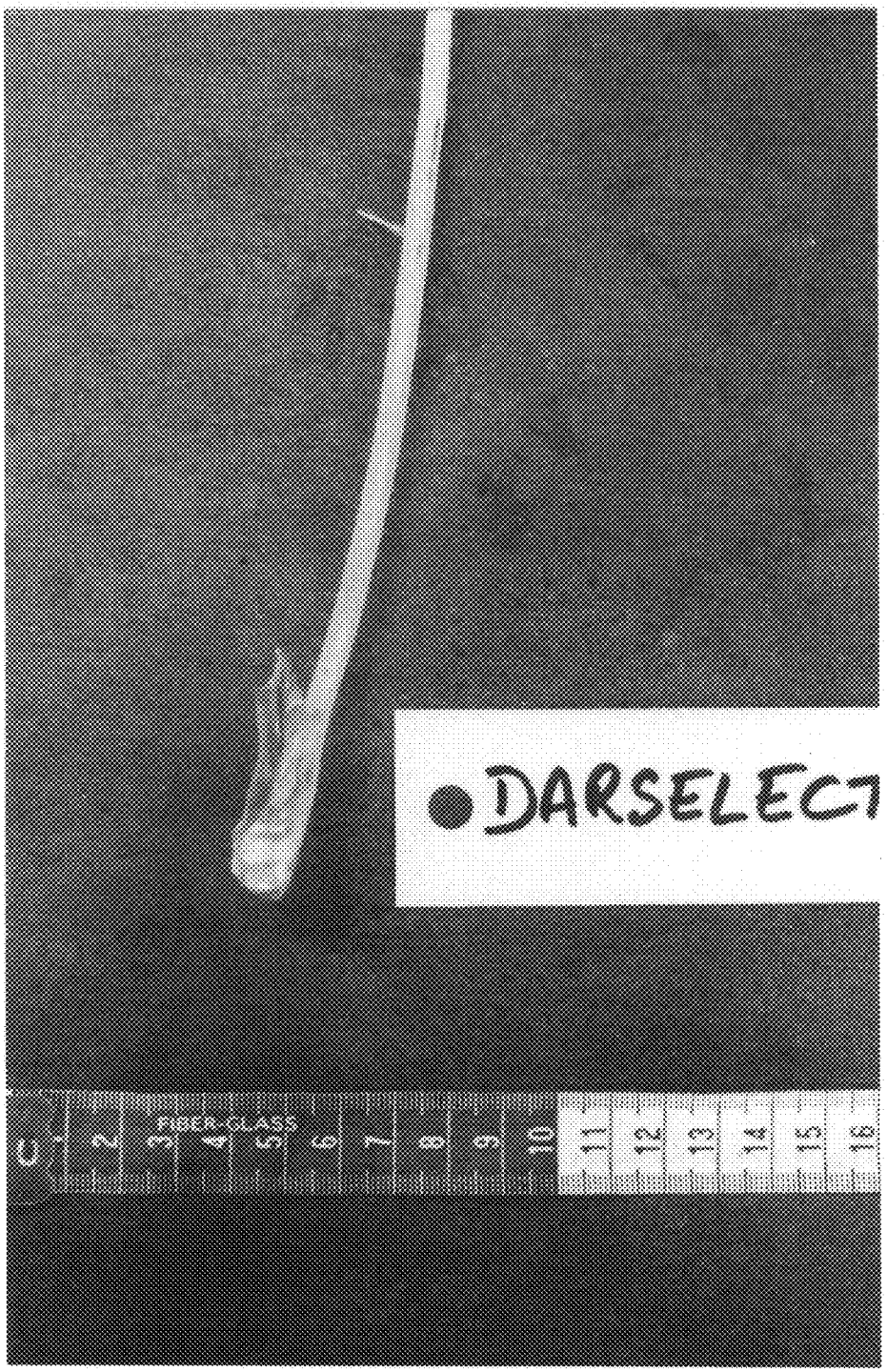
FIG. 7 shows the stipule and petiole of the variety 'Darselect'.
Figure 8:
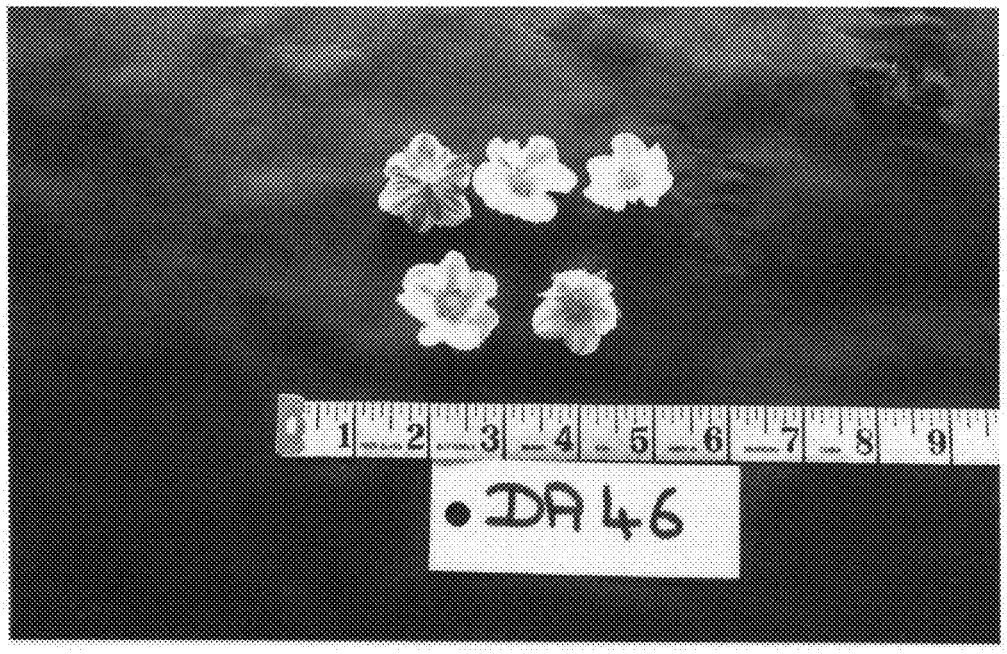
FIG. 8 shows the flower of the new variety, 'Deluxe'.
Figure 9:
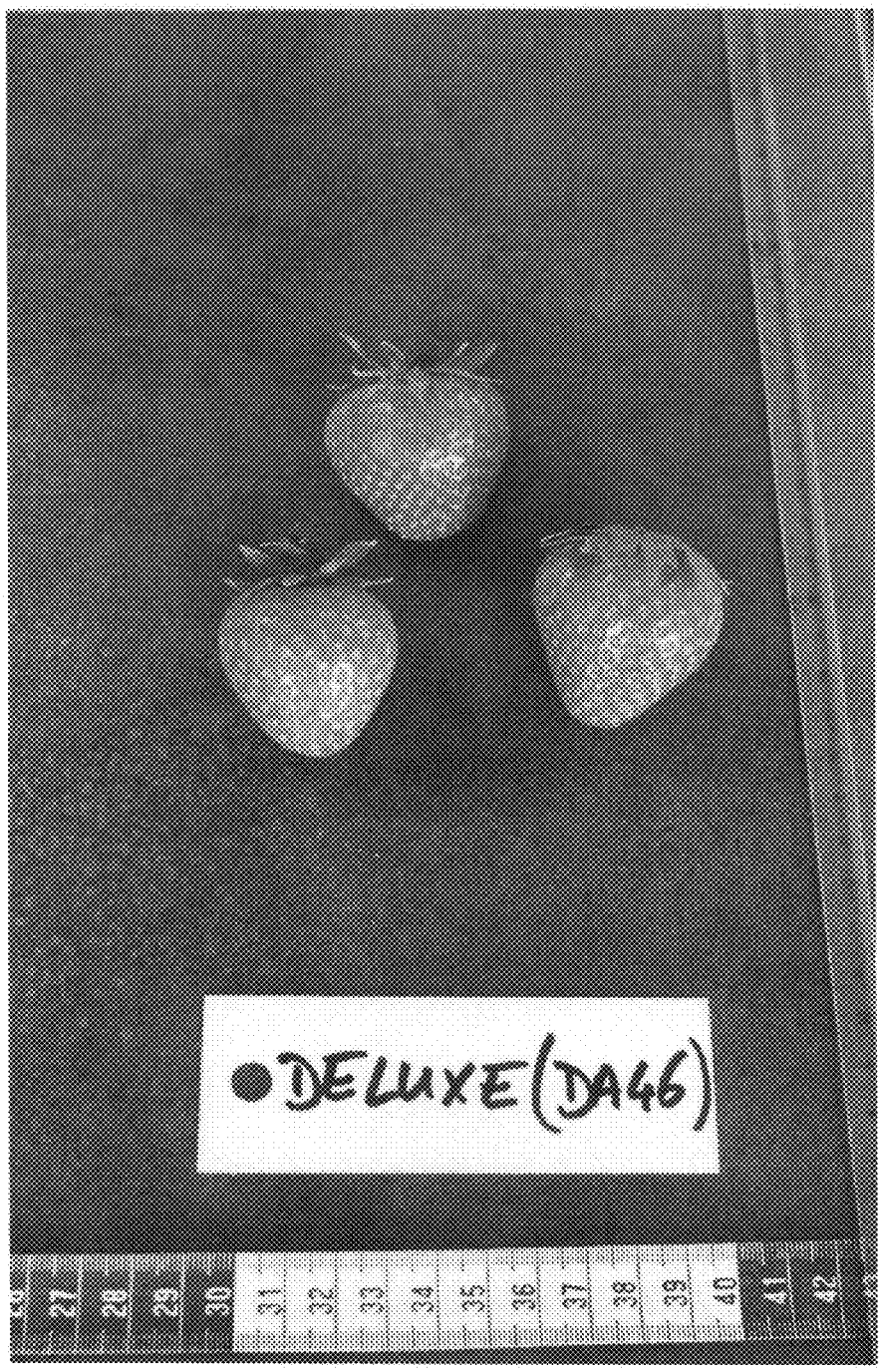
FIG. 9 shows typical whole fruit of the new variety 'Deluxe', illustrating the typical conical shape, orange red color (RHS orange-red group near 33 B to 33 A), and strong glossiness.
Figure 10:
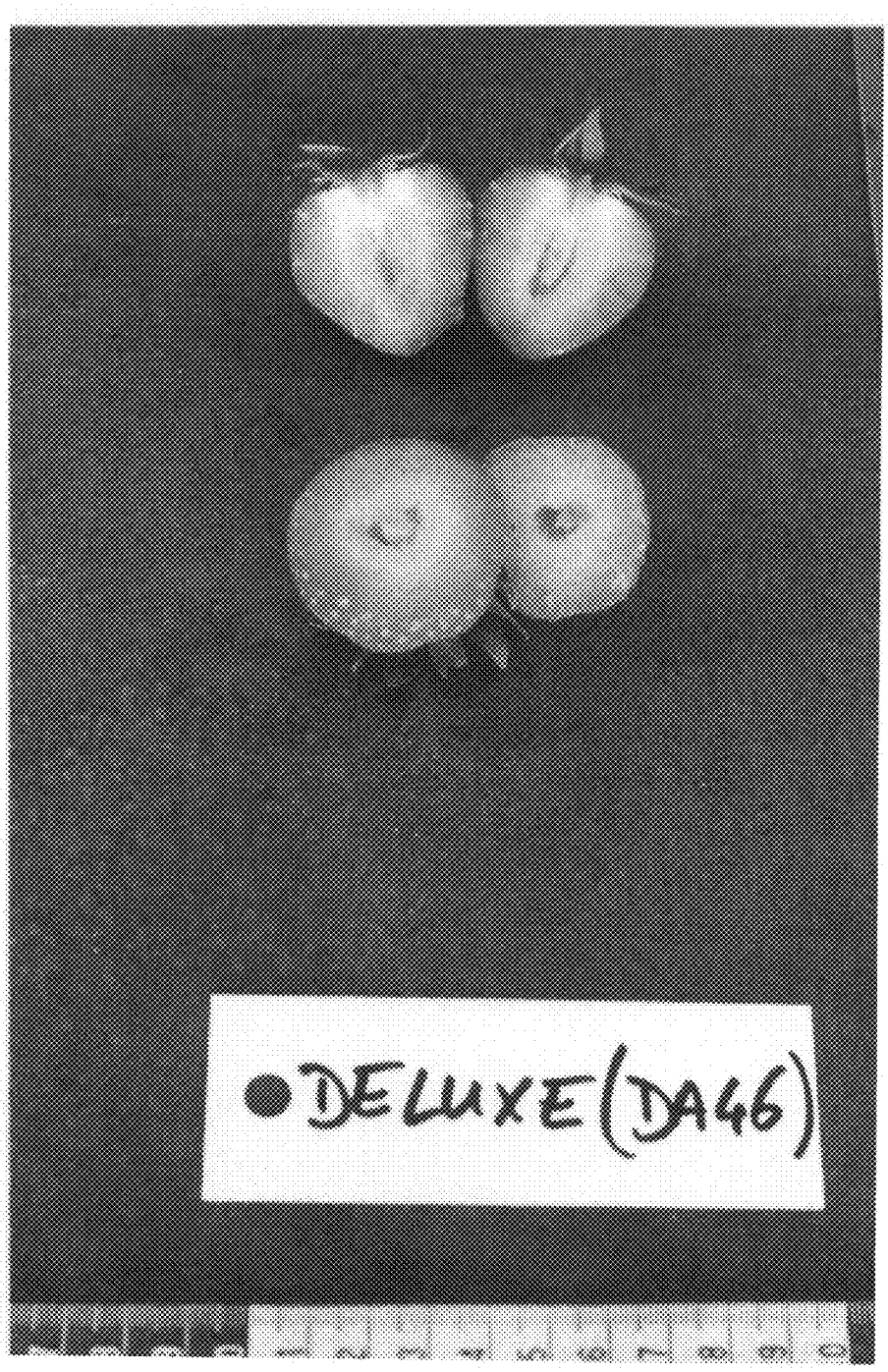
FIG. 10 shows a typical sliced section of the fruit of the new variety 'Deluxe', illustrating the typical flesh coloration of about orange red (RHS orange-red group near 32 C to 32 B) and a very weakly expressed hollow center.
Figure 11:
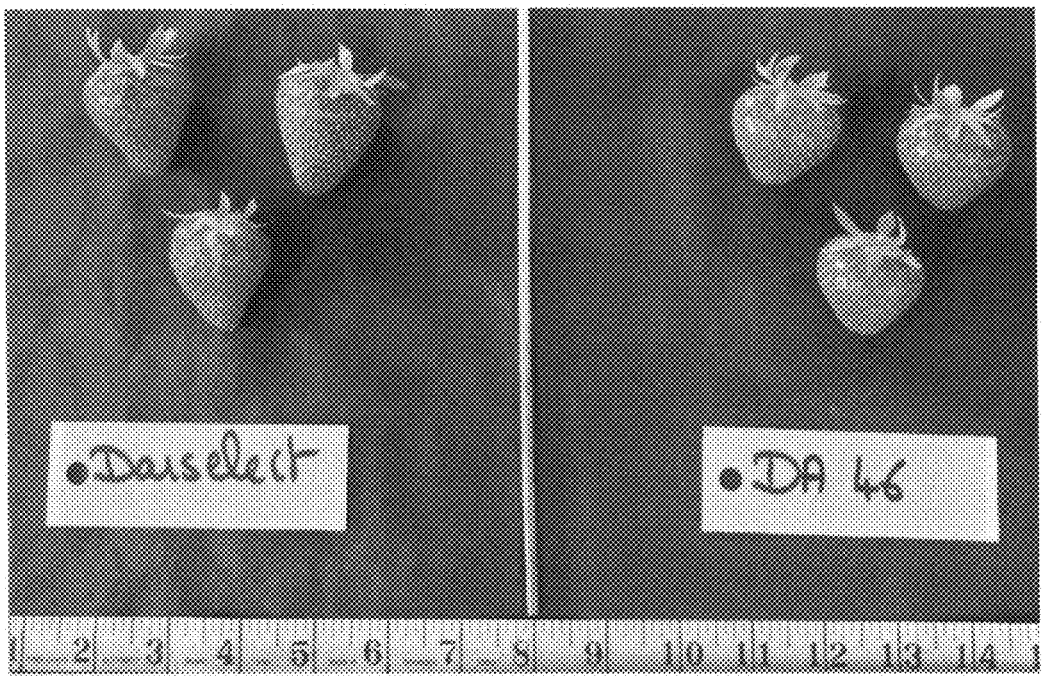
FIG. 11 shows a comparison of typical whole fruit of the new variety 'Deluxe' to that of the pollen parent 'Darselect', illustrating the typical round to conical shape of the fruit of the new variety.

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown in Le Barp, France 0.7° W., 44°, 50 meters elevation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface ondulation inherent to leaves and is generally a constant characteristic.

Table 1 shows the Weight (g/Fruit) at of the new variety 'Deluxe' on May 7 when compared to its pollen parent and closest variety 'Darselect' and the variety 'Clery'.

TABLE 1

| WEIGHT (g/fruit)[i] | May 7 |
|---|---|
| Deluxe | 32.4 |
| Darselect | 24.5 |
| Clery | 18.9 |

[i]WEIGHT is shown as the average weight per fruit in First Quality Fruits.

Table 2 shows a comparison of the fruit analysis between the new variety 'Deluxe' on May 7 when compared to its pollen parent and closest variety 'Darselect' and the variety 'Clery'.

TABLE 2

| | DELUXE | DARSELECT | CLERY |
|---|---|---|---|
| Humidity & Volatile Matter (%) | 92.7 | 91.5 | 91.5 |
| Dry Matter (%) | 7.3 | 8.5 | 8.5 |
| pH (to 20°) | 3.9 | 3.8 | 3.8 |
| Acidity as Anhydride Citric (%) | 0.6 | 0.6 | 0.6 |
| Soluble solids (°Brix) | 7.5 | 7.8 | 7.9 |
| Maturity Index | 12.5 | 13.0 | 13.2 |
| Dominant Tonality (nm) | 490 | 490 | 495 |
| Luminosity: Transmittance to 460 nm | 62.5 | 51.2 | 43.5 |

B. Dry Matter: It is the weight of the residual left from the trituration of the fruit after the drying process at a temperature of 103° C.$^{+}$2° C. until reaching constant weight.

$$\% \text{ Dry Matter} = \frac{\text{Weight Dry Matter}}{\text{Weight Fresh Matter}} \times 100$$

C. Humidity & Volatile Matter: Represents the content in volatile matters and water of the fruits.

$$(\%) \text{ Humidity \& Volatile Matter} = 100 - \% \text{ Dry Matter}$$

D. Maturity Index: Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

Plant:
- *Habit*.—Globose.
- *Growth habit*.—Upright.
- *Density*.—Dense.
- *Vigor*.—Strong.
- *Height*.—Long, about 35 cm.
- *Width*.—Medium to long, about 25 cm.
- *Number of crowns per plant*.—About 5 to 7 crowns per plant.

Stem:
- *Length*.—About 7 to 9 cm.
- *Pubescence*.—Slightly outwards.
- *Color*.—RHS yellow-green group (near 145 D to 145 C).

Leaf:
- *Size*.—Medium.
- *Color of upperside*.—Medium Green (RHS green group color near 139 A to 141 A).
- *Color of underside*.—RHS green group color (near 138 C to 139 D).
- *Cross section*.—Strong concave to slightly concave.
- *Blistering*.—Weak.
- *Glossiness*.—Medium.
- *Length*.—About 6 cm.
- *Width*.—About 10 to 12 cm.
- *Variegation*.—Absent.
- *Average serrations per leaf*.—About 16 to 18 serrations for each foliole (3 folioles per leaf).

Terminal leaflet:
- *Length/width ratio*.—Longer than broad.
- *Terminal leaflet shape of base*.—Acute.
- *Shape of incisions at margin*.—Serrate.
- *Length*.—Small, about 4 to 5 cm.
- *Width*.—Small, about 3 to 4 cm.

Petiole:
- *Attitude of hairs*.—Upwards.
- *Length*.—Medium, about 7 to 9 cm.
- *Diameter*.—About 2.0 to 2.5 mm.
- *Texture*.—Down and rigid.
- *Color*.—RHS yellow-green group (near 145 D to 145 C).
- *Pubescence*.—Slightly outwards.

Stipule:
- *Size*.—Absent or very small.
- *Anthocyanin coloration*.—Absent or very weak to weak. RHS greyed-orange group coloration (near 174 C to 174 B).
- *Length*.—About 8.0 to 9.0 mm.
- *Width*.—About 2.0 to 2.5 mm.

Stolons:
- *Number*.—Medium, about 5 to 7.
- *Antocyanin coloration*.—Weak. RHS yellow-green group (near 145 D to 145 C).
- *Pubescence*.—Medium.
- *Average diameter at the bract*.—Thin, about 2 to 3 mm.

Inflorescence:
- *Position relative to foliage*.—Level with.

Flower:
- *Size*.—Medium.
- *Size of calyx relative to corolla*.—Smaller.
- *Primary flower relative position of petals*.—Overlapping.
- *Average number of flowers per plant*.—About 50 to 55 flowers per plant.
- *Time from bloom to mature fruit* (*in Le Barp, France*).—About 38 to 43 days.
- *Diameter primary flowers*.—Medium, about 2.0-2.5 cm.
- *Diameter secondary flowers*.—Short, about 1.5-2.0 cm.
- *Diameter corolla primary flowers*.—About 2.0 to 2.5 cm.
- *Diameter corolla secondary flowers*.—About 1.5 to 2.0 cm.
- *Diameter calyx primary flowers*.—About 1.3 to 1.5 cm.
- *Diameter calyx secondary flowers*.—About 0.9 to 1.0 cm.
- *Color of receptacle*.—RHS orange-red group (near 33 B to 33 A).
- *Color of anthers*.—RHS yellow group (near 13 C to 13 B) and darkening with advanced maturity.
- *Pollen*.—Fertile and abundant.
- *Pollen color*.—RHS yellow orange group (near 15 B to 15 A).
- *Number of pistils*.—Numerous.
- *Pistil size*.—Generally average in size.
- *Pistil color*.—RHS yellow group (near 13C to 13 B).

Petal:
- *Length/width ratio*.—As long as broad.
- *Color*.—White (RHS white group near 155 D to 155 A).
- *Arrangement of the petals*.—Overlapping.
- *Length*.—Small, approximately 4 to 5 mm.
- *Width*.—Small, approximately 4 to 5 mm.
- *Texture* (*both sides*).—Smooth, soft and waved.
- *Number of petals per flower*.—Normally about 5.

Fruit:
- *Ratio of length/maximum width*.—Slightly longer than broad.
- *Size*.—Medium.
- *Fruit shape*.—Concial.
- *Difference in shapes between primary and secondary fruits*.—Moderate.
- *Band without achenes*.—Absent or very narrow.
- *Unevenness of surface*.—Weak.
- *Color*.—Orange red. (RHS orange-red group near 33 B to 33 A).
- *Evenness of color*.—Even.
- *Glossiness*.—Strong.
- *Insertion of achenes*.—Level with surface.
- *Insertion of calyx*.—Level with fruit.
- *Attitude of the calyx segments*.—Spreading.
- *Size of the calyx in relation to fruit diameter*.—Same size.
- *Adherence of calyx*.—Strong.
- *Firmness*.—Firm.
- *Color of flesh*.—Orange red (RHS orange-red group near 32 C to 32 B).
- *Hollow center*.—Absent or very weakly expressed.
- *Distribution of red colour of flesh*.—Marginal and central.
- *Time of flowering*.—Medium.
- *Time of ripening*.—Medium.
- *Type of bearing*.—Not remontant.
- *Peduncle length of inflorescence stem*.—Primary fruit about 20 to 25 cm, secondary fruit about 16 to 20 cm.
- *Primary fruit length*.—Medium, about 3.2 to 3.5 cm.
- *Primary fruit width*.—Medium, about 3.3 to 3.5 cm.
- *Secondary fruit length*.—Short, about 2.3 to 2.6 cm.

*Secondary fruit width*.—Short, about 2.2 to 2.5 cm.

*Color upperside of sepals*.—Yellow green group (near 145 D to 145 C).

*Color underside of sepals*.—Yellow green group (near 144 D).

*Length of sepals*.—Medium, about 4.0 to 6.0 mm.

*Width of sepals*.—Short, about 1.0 to 1.5 mm.

*Number of sepals per flower*.—The calyx presents 9 to 10 sepals with lanceolate shape and 3 to 4 sepals in addition smaller than above mencionated with less shape.

*Color of core*.—RHS orange-red group (near 32 D to 32C).

*Weight of fruit* (*Le Barp, May* 3).—27 g/fruit.

*Weight of fruit* (*Le Barp, May* 17).—20 g/fruit.

*Difference in shapes between primary and secondary fruits*.—Moderate.

*Band without achenes*.—Absent or very narrow.

*Color of achenes*.—RHS orange group (near 29 A to 30 D).

*Sweetness*.—Medium. 7.5° Brix.

*Acidity*.—Medium. 0.60% (Acidity as Anhydride Citric).

*Time of flowering* (50% *of plants at first flower*).—Medium.

*Time of ripening* (50% *of plants with ripe fruits*).—Medium.

*Type of bearing*.—Not remontant.

*Chilling*.—About 1000 hours.

Disease resistance: No particular sensitivity to any disease or parasite has been observed for 'Deluxe'.

Cold tolerance: As the capacity of plant to develop and to produce fruits below of 7° C. of temperature, the cold tolerance of 'Deluxe' is High.

Drought tolerance: Applicant has not made any test about drought tolerance.

What is claimed is:

1. A new and distinct strawberry plant of the variety substantially as shown and described.

* * * * *